United States Patent [19]

Endelson

[11] Patent Number: 5,722,439

[45] Date of Patent: Mar. 3, 1998

[54] DENTAL FLOSS DISPENSER ON CARD FORMAT

[76] Inventor: Robert A. Endelson, 41 Yates Ave., Atlantic Beach, N.Y. 11509

[21] Appl. No.: 607,113

[22] Filed: Feb. 26, 1996

[51] Int. Cl.$^6$ ............................................. A61C 15/00
[52] U.S. Cl. ......................... 132/321; 132/324; 132/329; 206/63.5
[58] Field of Search ........................ 132/321, 323, 132/324, 326, 327, 328, 329; 206/388, 104, 63.3, 63.5, 813; 433/143

[56] References Cited

U.S. PATENT DOCUMENTS

| | | | |
|---|---|---|---|
| 2,911,318 | 11/1959 | Lerch | 206/813 |
| 4,076,423 | 2/1978 | Russack | 206/63.5 |
| 4,327,755 | 5/1982 | Endelson | 132/324 |
| 4,630,729 | 12/1986 | Hirt et al. | 206/813 |
| 4,807,752 | 2/1989 | Chodorow | 206/63.5 |
| 4,881,560 | 11/1989 | Blank et al. | 132/324 |
| 5,160,077 | 11/1992 | Sticklin | 132/323 |
| 5,167,753 | 12/1992 | McCullough et al. | 132/323 |
| 5,322,077 | 6/1994 | Corella | 132/323 |
| 5,372,251 | 12/1994 | Thompson | 206/63.3 |

*Primary Examiner*—Gene Mancene
*Assistant Examiner*—Pedro Philogene

[57] ABSTRACT

A dental floss dispenser in a card format formed by a base panel having a shallow well surrounded by a peripheral ridge, and a face panel superposed on the base panel and bonded to the ridge. Adjacent the front end of the face panel are an aperture and a miniature cutting blade. Nested in the well is a supply of dental floss constituted by an unsupported flattened helical coil. The floss filament from which the coil is wound has a starting end at the front of the coil, the filament at the rear of the coil passing internally through the coil to emerge from its front as a pull out lead which is threaded through the aperture in the face panel. The starting end of the coil is bonded to adjacent convolutions and thereby prevent unwinding of the unsupported coil. To obtain a useable length of floss, the user pulls on the lead to partially unwind the coil and then cuts off the length on the blade. The bed of the well and a corresponding area on the inner surface of the top panel are each coated with a layer of pressure-sensitive adhesive which adheres to the convolutions of the nested coil to maintain its position and integrity. The tackiness of the pressure-sensitive adhesive is such that when the lead is pulled out to partially unwind the coil, the floss filament is then released from the adhesive coating layers.

13 Claims, 3 Drawing Sheets

DENTAL FLOSS DISPENSER ON CARD FORMAT

BACKGROUND OF INVENTION

1. Field of Invention

This invention relates generally to dental floss dispensers, and more particularly to a highly compact floss dispenser in a card format, making it possible to conveniently carry the dispenser in a wallet or elsewhere on the person.

2. Status of Prior Art

Dental disease is largely due to the accumulation of bacterial plaque on the teeth and gums. This plaque acts to generate acids which attack the teeth and gums, giving rise to tooth decay and caries, and resulting in periodontal disease. The therapeutic value of dental floss to dislodge debris collected between the teeth and to break up colonies of bacteria that gather near the gum line is well established.

Dental floss generally takes the form of a nylon, cotton or other filament of synthetic or natural fibers. Usually, the floss is waxed so that as the floss is extruded through a space between the teeth, its passage is lubricated. The advantage of dental floss is that it can traverse hard-to-reach places between the teeth and under bridges that are otherwise inaccessible to toothbrushes or other dental appliances. While toothpicks are sometimes used rather than dental floss, picks tend to impact debris between the teeth rather than to dislodge the debris.

Good dental hygiene dictates the use of floss after every meal so that food particles lodging between the teeth are not permitted to remain in these sites. Since the typical dental floss container or dispenser cannot be conveniently carried on the person, as a practical matter it is not feasible for most individuals to follow the dictates of good dental practice. Thus while these dispensers may be stored in household bathroom cabinets, an individual who wishes to apply dental floss away from home is faced with the problem of how best to carry a floss container in an inconspicuous manner.

Commercially-available dental floss dispensers are generally of the type disclosed in the Tarrson U.S. Pat. No. 4,162,688. This dispenser includes a box-like container having a reel of dental floss therein which is payed out through a top opening, the container being provided with a cutting blade so that a suitable length of dental floss may be separated from the supply. Because of the three-dimensional bulk of this boxlike dispenser, it cannot be conveniently carried in a jacket pocket or elsewhere on the person.

To overcome the practical drawbacks of existing types of dental floss dispensers, disclosed in the Endelson Pat. No. 4,327,755 is a dispenser in a credit card format, making it feasible to carry the dispenser in a wallet or billfold, or even in a shirt pocket without injury to the dispenser.

Because credit cards are currently in widespread use, most commercially available wallets incorporate flat slots or pockets adapted to accommodate credit cards without causing the wallet to bulge. Hence a dental floss dispenser in a credit card format may be stored inconspicuously in a wallet and put to use away from home under circumstances where dental floss is usually not available.

The dental floss dispenser in a credit card format disclosed in the Endelson '755 patent comprises a base panel having a peripheral ridge to define a shallow well within which is nested a supply of dental floss in flattened helical coil form. The leading end of the coil passes out of the well through an aperture and is caught by a lug adjacent an edge notch cut in the base panel. Anchored in the well is a blade whose cutting edge is exposed by the notch, whereby when floss is pulled out of the well to provide a usable length, it may then be cut by the blade. The dispenser is completed by a face panel bonded to the ridge to encapsulate the floss supply, the face panel having a corresponding notch.

A serious practical drawback of the dental floss dispenser disclosed in the Endelson '755 patent is that this dispenser is difficult and expensive to assemble. The supply of dental floss which must be deposited in the shallow well is an unsupported flattened coil which tends to fall apart unless carefully handled and this handling greatly complicates the assembly procedure.

To overcome this drawback, the Blank et al. Pat. No. 4,881,450 discloses a similar dental floss dispenser in a credit card format in which the flattened floss coil is housed within a plastic pouch. This pouch serves to maintain the integrity of the coil during the assembly process and also when the floss is being pulled out from the coil. Yet the floss dispenser disclosed in the '560 patent suffers from disadvantages, for the insertion of the unsupported flattened floss coil into a pouch does not lend itself to automation. This procedure must be carried out manually, thereby making the production of the dispenser labor-intensive and more expensive.

SUMMARY OF INVENTION

In view of the foregoing, the main object of this invention is to provide a dental floss dispenser in a card format which retains all of the advantages of similar dispensers disclosed in the '755 and '560 patents, yet overcomes their practical drawbacks whereby a dispenser in accordance with the invention can be assembled more easily and at lower cost and function more effectively than the prior art dispensers.

More particularly, an object of the invention is to provide a dental floss dispenser in a highly compact card format which includes internal coatings of pressure sensitive adhesive to maintain the integrity of the unsupported flattened coil of dental floss stored therein without however interfering with the partial unwinding of this coil when a length of floss is pulled out of the dispenser by its user.

Also an object of the invention is to provide in a dental floss dispenser of the above type an unsupported flattened helical coil of dental floss in which the floss filament from which the coil is wound has a starting end at the front of the coil, which filament at the rear of the coil then passes internally through the coil to emerge as a pull out lead at the front of the coil, the starting end of the filament being bonded to adjacent convolutions to prevent unwinding of the coil, whereby its integrity is maintained.

Yet another object of the invention is to provide a floss dispenser in a card format in which the pull out lead of the coil goes through an aperture in the card adjacent its front end, the card having an end slit leading into the aperture to facilitate entry of the lead into the aperture, which slit is thereafter sealed.

Briefly stated, in a preferred embodiment these objects are attained by a dental floss dispenser in a card format formed by a base panel having a shallow well surrounded by a peripheral ridge, and a face panel superposed on the base panel and bonded to the ridge. The face panel is provided adjacent its front end with an aperture and a miniature cutting blade. Nested in the well is a supply of dental floss constituted by an unsupported flattened helical coil. The floss filament from which the coil is wound has a starting end at the front of the coil, the filament at the rear end of the coil passing internally through the coil to emerge at the front as a pull out lead which is threaded through the aperture in the face panel.

The starting end of the coil is bonded to adjacent convolutions to prevent unwinding of the unsupported coil. To obtain a useable length of floss, the user pulls on the lead to partially unwind the coil and then cuts off the length on the blade. The bed of the well and a corresponding area on the inner surface of the top panel are each coated with a layer of pressure-sensitive adhesive which adheres to the convolutions of the nested coil to maintain its position and integrity. The tackiness of the pressure-sensitive adhesive is such that when the lead is pulled out to partially unwind the coil, the floss filament is then released from the adhesive layer.

BRIEF DESCRIPTION OF DRAWING

For a better understanding of the invention as well as other objects and further features thereof, reference is made to the following detailed description to be read in conjunction with the accompanying drawings, wherein.

DESCRIPTION OF INVENTION

Figure 1:
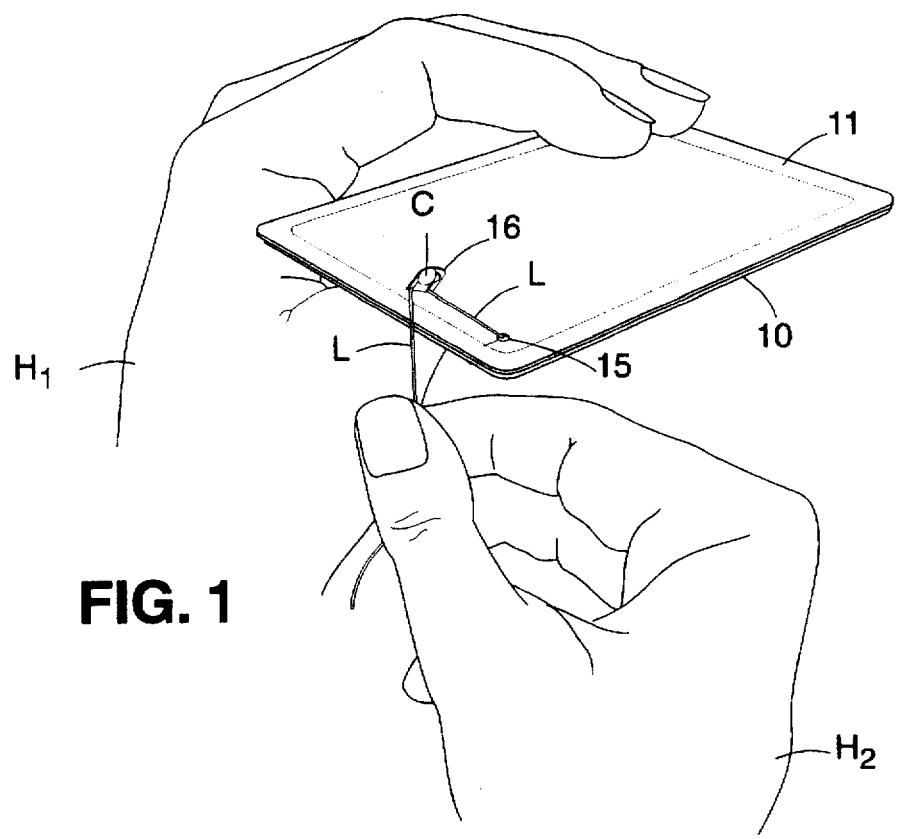
FIG. 1 is a perspective view of a preferred embodiment of a dental floss dispenser in a credit card format in accordance with the invention, the dispenser being held by the user in one hand, while a length of dental floss is pulled out of the dispenser and cut of by the other hand.
Figure 2:
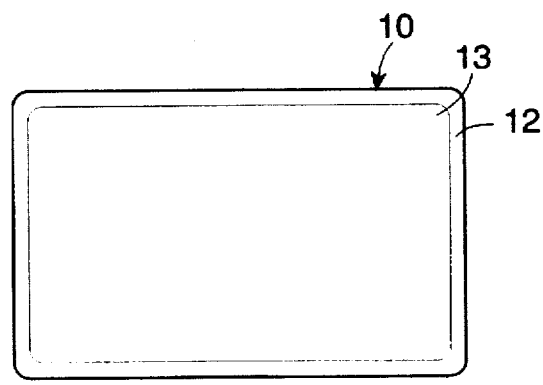
FIG. 2 is a rear view of the dispenser.
Figure 3:
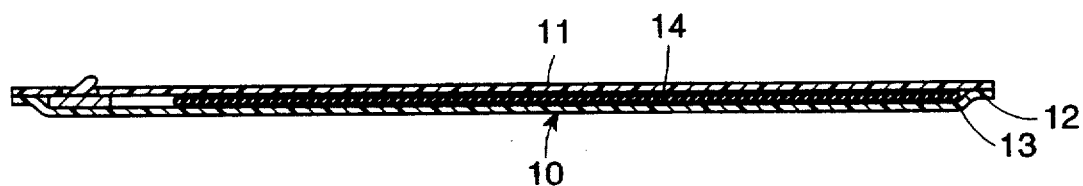
FIG. 3 is a longitudinal section taken through the dispenser.

Referring now to FIGS. 1 to 4, there is shown a dental floss dispenser in accordance with the invention in a credit card format, the dispenser including a rectangular base panel 10 and a complementary face panel 11 superposed thereon. Both panels are preferably fabricated of flexible synthetic plastic material such as polyvinyl chloride or other thermoplastic material. Typical credit card dimensions may be used for the panels, such as 3-⅛ and 2-⅛ inches. In practice, the card may be made in different dimensions, and be formed of other materials, such as coated paper or cardboard.

Base panel 10 is depressed to define a shallow rectangular well 13. Within well 13 peripheral ridge 12 is nested a supply of dental floss in the form of a flattened helical coil 14 of waxed dental floss. The preferred technique for fabricating the flattened helical coil is to wind the dental floss filament on a thin metal plate or mandrel whose dimensions are close to those of well 13. In practice the flattened coil may then pressed with a heated iron which acts to set and sinter the wax constituent of the floss whereby when the mandrel is withdrawn, the unsupported flattened coil retains its shape and may be easily placed within well 13.

Figure 4:
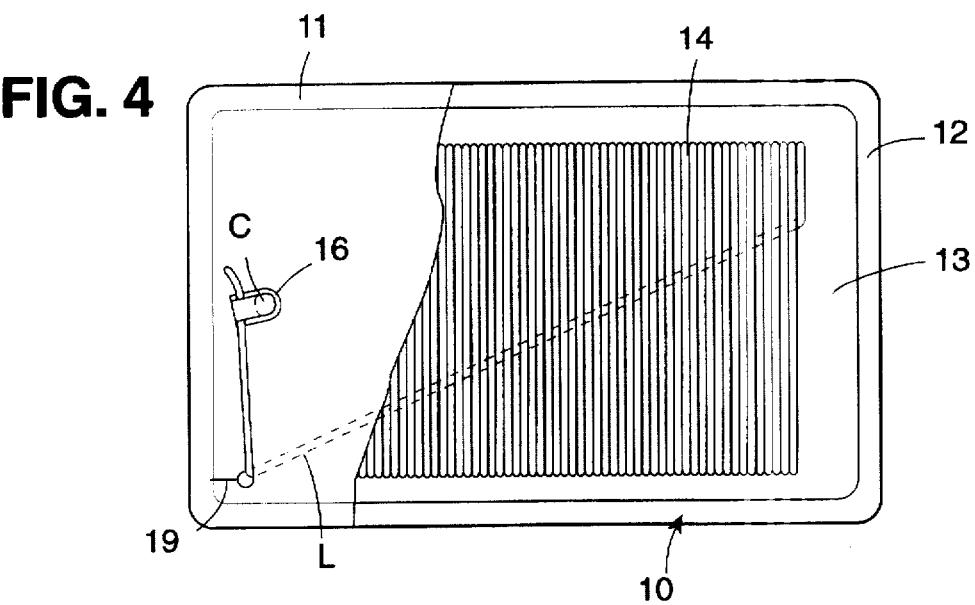
FIG. 4 is a top view of the dispenser with the face panel cut away to expose the flattened floss coil nested in the well of the base panel.
Figure 5:
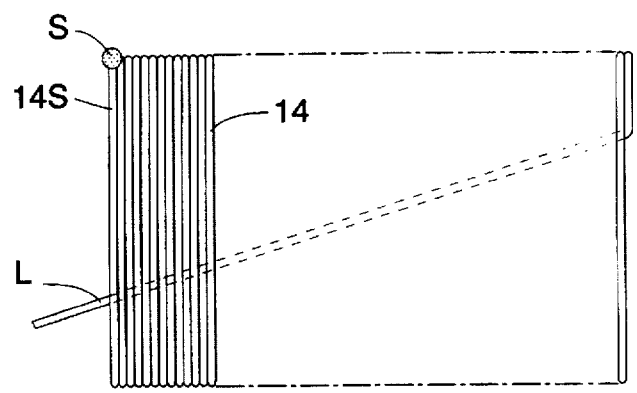
FIG. 5 shows the front end portion of the flattened coil to which a spot of adhesive is applied to prevent unwinding of the coil.
Figure 8:
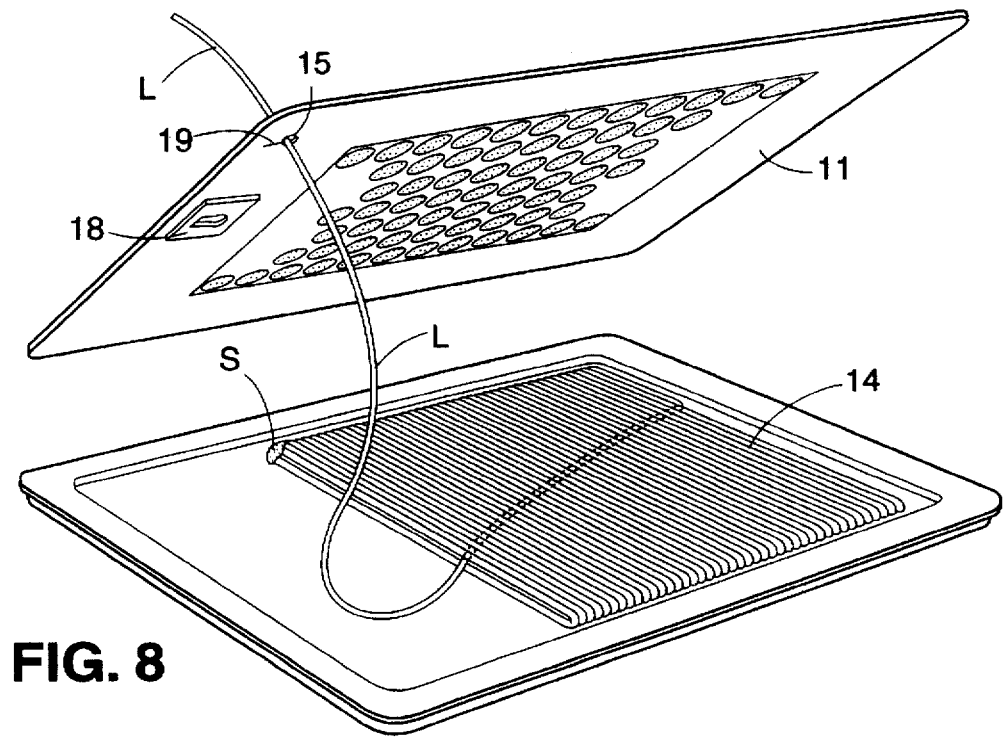
FIG. 8 is a perspective view of the dispenser in which the top panel is raised above the base panel to expose the flattened coil nested in the well of the base panel.

As best seen in FIGS. 4, 5 and 8, flattened coil 14 is constituted by a helically wound floss filament whose starting end 14S is at the front of the coil. This wound filament when, it reaches the rear of the coil, is then passed internally through the coil to emerge from its front as a pull out lead L which when pulled, by a user proceeds to unwind the coil from the rear toward the front. Thus as the coil is unwound it proceeds to shrink in length. Lead L is threaded through a small aperture 15 adjacent the left corner in face panel 11 at the front end of the card.

Figure 6:
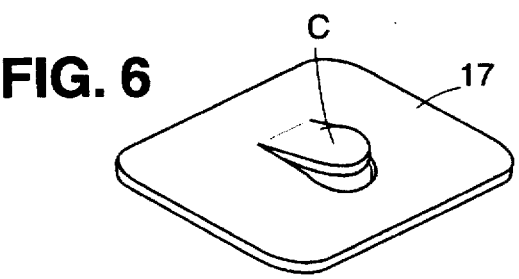
FIG. 6 is a separate view of the cutting blade element of the dispenser.
Figure 7:
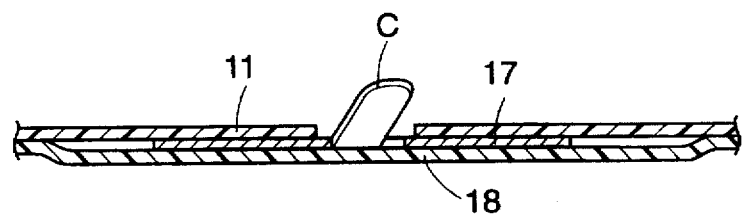
FIG. 7 is a section taken through the face panel of the card showing how the cutting blade element is attached thereto.

Projecting through an opening 16 die cut in the face panel 11 at the center of its front end is a miniature cutting blade 6 that is mounted on a small rectangular plate 17, as shown in FIGS. 6 and 7. Plate 17 is placed against the underside of face panel 11 and secured thereto by a strip 18 of adhesive tape.

When the dispenser is put to use, then as shown in FIG. 1, the user holds the card in one hand $H_1$, and with the fingers of his other hand $H_2$, pulls lead L out of aperture 15 to a desired floss length. He then loops the filament about cutting blade 6 and cuts off this length.

The starting end 14S of the floss filament from which coil 14 is wound, as shown in FIGS. 5 and 8 has a blob (S) of adhesive applied thereto which bonds the starting end to adjacent convolutions of the coil and thereby prevents it from unravelling. The rear of the coil is prevented from unravelling because the filament at the rear end passes through the coil to emerge as the pull out lead L at the front. Hence though the flattened coil is unsupported, it will not fall apart in the course of its transfer from a mandrel to the well in the base panel.

In practice, instead of a blob of adhesive, the starting end 14S of the filament may be thermally bonded to adjacent convolutions to prevent the coil from unravelling.

Figure 9:
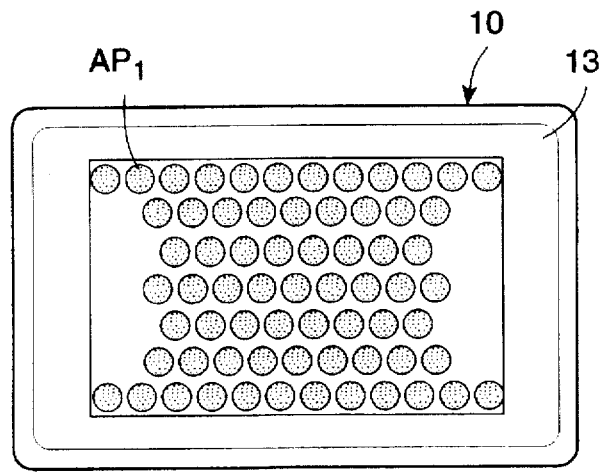
FIG. 9 shows the pattern of the pressure-sensitive adhesive layer coated the bed of the well in the base panel of the card.

In order to maintain the integrity of the flattened coil and its proper position in the well 13 of the base panel, the bed of well 13 of the base panel 10, as shown in FIG. 9, is coated with a layer of pressure-sensitive adhesive in a grid-like pattern $AP_1$. This pattern is formed by an array of circular holes which are free of adhesive, so that the adhesive exists only in the network of lands interconnecting the holes.

Figure 10:
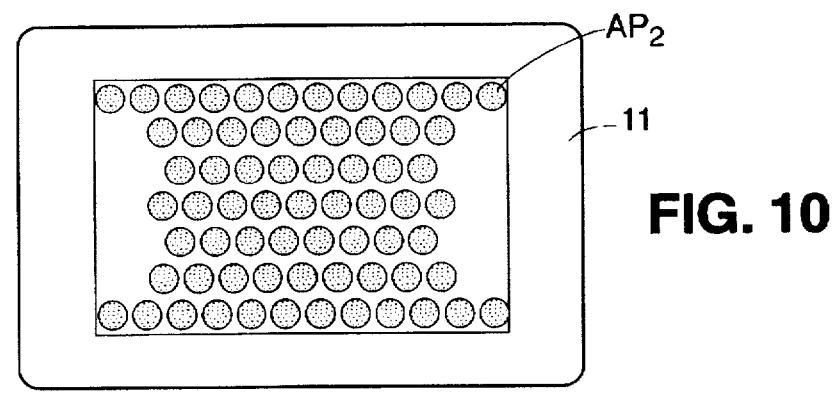
FIG. 10 shows the pattern of the pressure-sensitive adhesive layer coated on a corresponding inner surface of the face panel.

As shown in FIG. 10, the area of the inner surface of face panel 11 which corresponds to the bed of the well is coated with a layer of pressure-sensitive adhesive in a grid-like pattern $AP_2$ which matches pattern $AP_1$.

When face panel 11 is peripherally bonded to base panel 10 to complete the structure of the dispenser, flattened coil 14 is then encapsulated therein and is thereby sealed to maintain its hygienic condition. Coil 14 is then sandwiched between the adhesive layer $AP_2$ on the inner surface of the face panel and the like adhesive layer $AP_1$ on the bed of the well in the base plate.

The pressure-sensitive adhesive used on these layers is preferably a water-based acrylic composition whose density and tackiness characteristics are such that the adhesive in contact with the convolutions of the flattened coil on both sides thereof lightly adheres thereto to maintain the integrity of the coil and prevent its displacement. But when lead L is pulled out to draw a length of floss filament from the flattened coil, the coil is then partially unwound from the rear thereof to an extent depending on the length pulled out by the user.

As the coil is being partially unwound, the unwinding convolutions thereof in contact with the pressure-sensitive adhesive layers are then released, with no adhesive remaining on these convolutions. Hence the length of floss withdrawn from the dispenser is free of adhesive and is not contaminated thereby. The characteristics of the pressure-sensitive adhesive must be such as to adhere to the convolutions of the nested supply without however sticking to these convolutions when they are pulled away from the adhesive layers.

When the dispenser is being assembled, it is necessary to thread lead L into aperture 15 adjacent one corner at the front end of the face panel 11. To facilitate entry into this aperture, a slit 19 is cut in the face panel that extends from the front end of the panel to aperture 15. In order, therefore, to thread lead L into aperture 15, the lead is drawn edgewise through the slit 19 into the aperture. Since the face panel 11 is formed of thermoplastic material, as is the base panel 10, when the face panel is bonded by heat and pressure to the peripheral ridge 12 of the base panel, this action serves also to seal slit 19.

While a floss dispenser in a card format in accordance with the invention is essentially planar and highly compact, being not much thicker than a standard credit card, it is nevertheless capable of encapsulating a substantial supply of dental floss, and is therefore not quickly exhausted, but may be put to repeated use.

A significant advantage of a dental floss dispenser in accordance with the invention is that it may be personalized and printed under computer control with the names of individuals derived from the computer memory and with the business title of an advertiser, very much in the manner of existing credit cards. Hence such printed floss dispensers may be distributed as advertising premiums that are likely to be treasured by recipients. Or such printed dental floss dispensers may be given away by restaurants and other establishments rather than match books, for there is diminishing interest in the latter, because of the prevalence of disposable butane lighters.

While there has been shown and described a preferred embodiment of a dental floss dispenser in accordance with the invention, it will be appreciated that many changes and modifications may be made therein without, however, departing from the essential spirit of the invention.

Thus instead of nesting the dental floss flattened coil supply in a well in the base panel, the supply may be sandwiched between the base panel and the face panel to occupy a cavity defined between these superposed panels which are peripherally bonded together to enclose the supply.

In a floss dispenser in this format, the supply sandwiched between the panels is adhered thereto by a pressure-sensitive adhesive layer coated on the inner surface of either the base panel or the face panel, or on both panels.

I claim:

1. A dental floss dispenser in a card format comprising:
A. a base panel having a shallow well surrounded by a peripheral ridge;
B. a face panel superposed on the base panel and bonded to the ridge, said face panel having adjacent the front end an aperture and a miniature cutting blade; and
C. a supply of dental floss nested in said well, said supply being constituted by an unsupported flattened helical coil which is wound of a floss filament whose starting end is at the front of the coil, and is bonded to an adjacent convolution to prevent unravelling of the coil, the filament when reaching the rear of the coil then passing internally through the coil to emerge from the front of the coil as a pull out lead which is threaded through said aperture so that a length thereof may be withdrawn for use and cut off by the cutting blade, said well having a bed coated with a layer of pressure-sensitive adhesive which makes contact with the convolutions of the flattened coil nested in the well to maintain the position and integrity of the coil, the convolutions being released from the adhesive layer when the lead of the coil is pulled.

2. A dispenser as set forth in claim 1, in which an undersurface of said face panel in an area corresponding to that of the bed is coated with a layer of pressure-sensitive adhesive which makes contact with the convolutions of the flattened coil whereby the coil is sandwiched between the bed and the face panel layer.

3. A dispenser, as set forth in claim 1, in which the starting end is thermally bonded to adjacent convolutions.

4. A dispenser as set forth in claim 1, in which the face panel is provided with a slit extending from its front end of to the aperture to facilitate entry of the filament into the aperture.

5. A dispenser as set forth in claim 1, in which the card is of credit card size.

6. A dispenser as set forth in claim 1, in which the face panel and the base panel are both formed of thermoplastic, synthetic plastic material and are thermally bonded together.

7. A dispenser as set forth in claim 6, in which the material is polyvinyl chloride.

8. A dispenser as set forth in claim 1, in which the pressure-sensitive adhesive has tacky characteristics such that the adhesive lightly adheres to the convolutions of the coil in contact therewith, whereby when the lead is pulled to partially unwind the coil, the convolutions are then released from and are free of the adhesive.

9. A dispenser as set forth in claim 1, in which the pressure-sensitive adhesive layer is in a grid pattern having an array of openings which are free of adhesive, the adhesive being in a network of lands interconnecting the openings.

10. A dispenser as set forth in claim 1, in which the floss filament is formed of waxed nylon.

11. A dental floss dispenser in a card format comprising:
A. a base panel;
B. a face panel superposed on the base panel and peripherally bonded thereto to define an interior cavity between the panels, said face panel having adjacent the front end and aperture and a miniature cutting blade; and
C. a supply of dental floss disposed in said cavity and sandwiched between the panels, said supply being constituted by an unsupported flattened helical coil which is wound of a floss filament whose starting end is at the front of the coil, and is bonded to an adjacent convolution to prevent unravelling of the coil, the filament when reaching the rear of the coil then passing internally through the coil to emerge from the front of the coil as a pull out lead which is threaded through said aperture so that a length thereof may be withdrawn for use and cut off by the cutting blade, an inner surface of at least one of the panels being coated with a layer of pressure-sensitive adhesive which makes contact with the convolutions of the flattened coil in the cavity to maintain the position and integrity of the coil, the convolutions being released from the adhesive layer when the lead of the coil is pulled.

12. dispenser as set forth in claim 11, in which the inner surface of both panels is coated with a layer of pressure-sensitive adhesive.

13. A dispenser as set forth in claim 11, in which the starting end of the coil is thermally bonded to adjacent convolutions thereof to prevent the unravelling of the front of the coil.

* * * * *